United States Patent
Hitce

(10) Patent No.: US 11,318,079 B2
(45) Date of Patent: May 3, 2022

(54) POLYHYDROXYLATED (1-PHENYL-2-PHENYL) ETHYLENE DERIVATIVES AS AN ANTI-AGEING AND PHOTOPROTECTIVE AGENT

(71) Applicant: L'OREAL, Paris (FR)

(72) Inventor: Julien Hitce, Aulnay-sous-Bois (FR)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 15/576,555

(22) PCT Filed: May 27, 2016

(86) PCT No.: PCT/EP2016/062061
§ 371 (c)(1),
(2) Date: Nov. 22, 2017

(87) PCT Pub. No.: WO2016/189153
PCT Pub. Date: Dec. 1, 2016

(65) Prior Publication Data
US 2018/0153785 A1 Jun. 7, 2018

(30) Foreign Application Priority Data
May 27, 2015 (FR) ...................... 1554754

(51) Int. Cl.
| A61K 8/37 | (2006.01) |
| A61K 8/34 | (2006.01) |
| A61Q 19/08 | (2006.01) |
| A61K 8/33 | (2006.01) |
| A61Q 17/04 | (2006.01) |

(52) U.S. Cl.
CPC .................. *A61K 8/37* (2013.01); *A61K 8/33* (2013.01); *A61K 8/347* (2013.01); *A61Q 19/08* (2013.01); *A61Q 17/04* (2013.01)

(58) Field of Classification Search
None
See application file for complete search history.

(56) References Cited

U.S. PATENT DOCUMENTS

| 6,147,121 | A | * | 11/2000 | Breton | A61K 8/347 514/726 |
| 6,814,960 | B1 | * | 11/2004 | Holzl | A01N 31/08 424/65 |
| 2006/0003033 | A1 | * | 1/2006 | McClellan | A61K 31/565 424/729 |
| 2008/0139650 | A1 | * | 6/2008 | Jakob | A01N 31/08 514/557 |
| 2009/0074501 | A1 | * | 3/2009 | Miller | A45D 19/02 401/129 |
| 2010/0247587 | A1 | * | 9/2010 | Cebrian Puche | A61Q 19/04 424/401 |
| 2013/0203688 | A1 | * | 8/2013 | Barbeau | A61K 31/085 514/25 |
| 2013/0259815 | A1 | * | 10/2013 | Loy | A61K 8/0212 424/62 |
| 2013/0315848 | A1 | * | 11/2013 | Beck | A61K 8/347 424/60 |

FOREIGN PATENT DOCUMENTS

| EP | 0953346 | A | 11/1999 |
| FR | 2777183 | A1 | 10/1999 |
| FR | 2777186 | A | 10/1999 |
| IN | 201103045 | I4 * | 6/2013 |
| JP | H08175960 | A | 7/1996 |
| WO | 2004/005098 | A1 | 1/2004 |
| WO | WO-2014048868 | A2 * | 4/2014 ............... A61K 8/27 |

OTHER PUBLICATIONS

Ramos-e-Silva et al. Clinics in Dermatology 2013 31:750-758 (Year: 2013).*
PCT International Search and Written Opinion, 11 pgs, Jan. 2017.
A.K. Saha, et al., "AMPK Regulation of the Growth of Cultured Human Keratinocytes," ScienceDirect, Biochemical and Biophysical Research Communications 349, 2006, pp. 519-524.

* cited by examiner

*Primary Examiner* — Robert A Wax
*Assistant Examiner* — Caralynne E Helm
(74) *Attorney, Agent, or Firm* — McNees Wallace & Nurick LLC

(57) ABSTRACT

The present invention is directed towards the cosmetic use of at least one compound of formula (I) and/or solvates thereof and/or stereoisomers thereof:

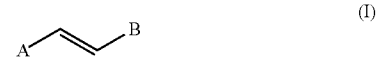

(I)

in which groups A and B are different and:
A-* represents a disubstituted phenyl radical:

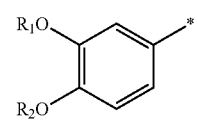

B-** represents a mono- or disubstituted phenyl radical:

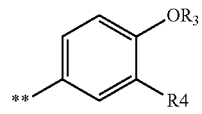

or of a composition comprising, in a physiologically acceptable medium, at least one compound of formula (I), for treating and/or preventing the signs of ageing and/or of photoageing of keratin materials, preferably of the skin.

25 Claims, No Drawings

POLYHYDROXYLATED (1-PHENYL-2-PHENYL) ETHYLENE DERIVATIVES AS AN ANTI-AGEING AND PHOTOPROTECTIVE AGENT

The present invention relates to the use of non-symmetrical 1-phenyl(3,4-substituted)-2-phenyl(3,4-substituted) ethylene compounds of formula (I) for treating and/or preventing the signs of skin ageing and/or as a photoprotective agent for keratin materials; it also relates to novel symmetrical 1-phenyl(3,4-substituted)-2-phenyl(3,4-substituted) ethylene compounds of formula (II).

Human skin is made up of three compartments, namely a superficial compartment, which is the epidermis, the dermis, and a deep compartment, which is the hypodermis.

The dermis provides the epidermis with a solid support. It is also its nourishing element. It is mainly constituted of fibroblasts and an extracellular matrix (ECM).

This extracellular matrix is constituted of various macromolecules responsible for the mechanical strength of the skin, for its suppleness, for its tonicity and for its elasticity, and also for the important physiological functions (moisturization, thermoregulation and regulation of skin permeability). Among these macromolecules are in particular collagens, elastin and glycoconjugates (glycoproteins and proteoglycans).

Collagens represent 70% of the ECM proteins. In the skin, numerous types of collagen constitute the ECM, including in particular the interstitial collagens (type I, II, III collagens) of fibrillar structure, produced essentially by the fibroblasts, and responsible for the cohesion, the rigidity and the mechanical strength, the collagens of the basal lamina (type IV collagens) synthesised by the adjacent cells and in the skin by the keratinocytes and which play in particular a mechanical role, and the collagens which form fibrils for anchoring of the basal membrane (dermis-epidermis link) expressed by the epidermal keratinocytes (type VII collagens).

It is also known that collagen synthesis begins with the assembly of procollagen units. For example, for the synthesis of collagen type I, these are units of procollagen type I (also called Pro-Coll1).

Naturally, collagen fibres are constantly renewed, but this renewal decreases with age, which leads to thinning of the dermis.

In addition, glycation is a non-enzymatic process involving a saccharide (glucose or ribose) which reacts via the Maillard reaction with an amine group of an amino acid residue (for instance lysine), particularly an amino acid residue of a protein, to form a Schiff's base. This base, after an "Amadori" molecular rearrangement, may lead, via a succession of reactions, to bridging, particularly intermolecular bridging, for instance of pentosidine type.

This phenomenon is characterized by the appearance of glycation products, the content of which increases uniformly as a function of age. Glycation products are, for example, pyrraline, carboxymethyllysine, pentosidine, crossline, $N^e$(2-carboxyethyl)lysine (CEL), glyoxal-lysine dimer (GOLD), methylglyoxal-lysine dimer (MOLD), 3DG-ARG imidazolone, versperlysines A, B, C, threosidine, or advanced glycosylation end products (or AGEs).

The glycation of proteins is therefore a universal phenomenon, well known in the skin, particularly at the level of the collagen fibres. The glycation of collagen in fact increases uniformly with age, leading to a uniform increase in the content of glycation products in the skin.

Without wishing to introduce any theory of ageing of the skin, it should be noted that it has been possible to demonstrate during skin ageing other changes in collagen which might also be a consequence of glycation, such as a decrease in heat denaturation, an increase in resistance to enzymatic digestion and an increase in intermolecular bridging (Tanaka S. et al., 1988, J. Mol. Biol., 203, 495-505; Takahashi M. et al., 1995, Analytical Biochemistry, 232, 158-162). Furthermore, glycation-mediated changes in certain constituents of the basal membrane such as collagen IV, laminin and fibronectin were able to be demonstrated (Tarsio J F. et al., 1985, Diabetes, 34, 477-484; Tarsio J F. et al., 1988, Diabetes, 37, 532-539; Sternberg M. et al., 1995, C. R. Soc. Biol., 189, 967-985).

It is thus understood that, in the course of ageing of the skin, the physicochemical properties of collagen become modified and collagen becomes more difficult to dissolve and more difficult to degrade. A stiffening of the tissues follows, resulting essentially in a loss of skin tonicity.

Moreover, the skin changes due to intrinsic ageing are the consequence of genetically programmed senescence in which endogenous factors are involved. This intrinsic ageing causes in particular a slowing of skin cell renewal, which is essentially reflected by the occurrence of clinical modifications such as a reduction in subcutaneous adipose tissue and the appearance of fine wrinkles or fine lines, and by histopathological changes such as an increase in the number and thickness of elastic fibres, a loss of vertical fibres of the elastic tissue membrane, and the presence of large irregular fibroblasts in the cells of this elastic tissue. The epidermis, which constitutes the upper layer of the skin, is undergoing constant regeneration. The epidermis is constituted of several layers of cells, the deepest of which is the basal layer constituted of undifferentiated cells. Over time, these cells will differentiate and migrate to the surface of the epidermis while constituting the various layers thereof, until they form, at the surface of the epidermis, the corneocytes which are dead cells that are eliminated by the natural phenomenon of desquamation. This loss at the surface is compensated for by the migration of cells from the basal layer towards the surface of the epidermis. There is perpetual renewal of the skin. The epidermis is therefore constantly engaged in producing new keratinocytes to compensate for the continuous loss of epidermal cells at the horny layer. However, in the course of ageing, a decrease in the number of cells in the proliferation phase, and consequently a decrease of the live epidermal layers, may be observed physiologically.

The homeostasis of the skin, and in particular of the epidermis, results from a finely regulated balance between the processes of proliferation and of differentiation of the skin cells. These processes of proliferation and differentiation are entirely regulated: they participate in the renewal and/or regeneration of the skin and lead to the maintenance of a constant thickness of the skin, and in particular of a constant thickness of the epidermis. This homeostasis of the skin also participates in maintaining the mechanical properties of the skin.

However, this homeostasis of the skin may be impaired by certain physiological factors (age, menopause, hormones, etc.) or environmental factors (UV stress, oxidative stress, irritant stress, etc.).

The proliferative cells are metabolically very active and are sensitive to these deleterious factors (intrinsic or environmental), with, as a consequence on the epidermis, a reduction in their amount. It is thus important to preserve these cells in order to contribute towards delaying the onset of the signs of ageing.

The cellular vitality of the keratinocytes may be decreased especially in the context of ageing or on account of oxidative stress (for example solar radiation, i.e. UV, visible light, infrared), on account of attack on the epidermis by toxins or metabolites of the microflora, or, more generally, during chronological ageing. The capacity for renewal and differentiation of the keratinocytes is reduced and the homeostasis of structures dependent thereon, such as the barrier function of the epidermis, is impaired.

When the regenerative potential of the epidermis becomes smaller: the cells of the basal layer divide less actively, leading especially to a slowing-down and/or decrease in epidermal renewal. Consequently, the cell renewal no longer compensates for the loss of cells removed at the surface, leading to atrophy of the epidermis and/or a reduction in skin thickness.

Impairments in epidermal homeostasis are also reflected by a dull and/or off-colour appearance of the skin complexion.

Impairment of the barrier function is manifested by various signs depending on the localization: hyperkeratosis, thin epidermis, surface wrinkles.

The signs associated with impairment of the cellular vitality of the epidermis thus concern not only its structure, but also its homeostasis. The resistance to stress of the epidermis and its capacity for regeneration are reduced. If the skin barrier of an elderly person is compared with that of a young adult, the differences do not appear at first sight: the thickness of the horny layer and the composition of its lipids are not necessarily altered, and the barrier function is conserved. The deficiencies of the elderly skin barrier appear under mechanical stress or during exposure to irritant factors: the barrier of an elderly epidermis degrades more rapidly and its function recovers less quickly. On a daily basis, actions such as alcoholic disinfection, or contact with lemon juice then cause discomfort, and dry air is poorly tolerated, whereas young skin tolerates this without any problem.

These aesthetic signs such as wrinkles, fine lines, etc. are such that there is a need in cosmetics for compounds acting on the skin to improve the cellular vitality when it is impaired.

AMPK is present in all the cells of the body and plays an energy gauge role therein. AMPK (or 5'-adenosine monophosphate activated protein kinase) is a heterotrimeric enzyme composed of a catalytic subunit a with kinase activity and two regulatory subunits β and γ. The activity of AMPK depends on the variation of the AMP/ATP ratio which characterizes the energy level of the cell (ATP being hydrolyzed into AMP to "deliver" the energy required for the various biochemical processes of the cell). It is present in two forms, phosphorylated or non-phosphorylated, the phosphorylated form being the active form.

When it is activated in response to an energy demand or a stress of the cell, AMPK increases the energy-generating processes such as glycolysis and it inhibits the non-essential consuming processes, thus enabling cell survival. Preservation of the cellular energy status is involved in maintaining the longevity of the species and combatting the signs of ageing. Thus, compounds that are capable of increasing the activity of AMPK are at the present time the object of great interest in the treatment of age-related clinical manifestations. The value in transposing this approach, validated for the whole organism, to the skin in the context of preventing its age-related impairment may be understood.

The AMPK activity corresponds to the cellular concentration of phosphorylated AMPK. Thus, it is worthwhile having the highest possible levels of phosphorylated protein in order to have this high activity.

The role of AMPK in controlling the energy metabolism of the keratinocyte is suspected at the present time (www.ncbi.nlm.nih.gov/pubmed/19096122?ordinalpos=2&itool=EntrezSystem2.PEntrez.Pubmed.Pubmed_ResultsPanel.Pubmed_DefaultReportPanel.Pubmed_RVDocSumPrahl S & al. Biofactors. 2008; 32(1-4):245-55), its involvement in the proliferation and differentiation of the keratinocyte has been established (Saha AK et al. Biochem Biophys Res Commun. 2006 Oct 20; 349(2): 519-24).

WO 2004/05098 proposes to modulate the lifetime of any cell or of an organism by controlling the activity of AMPK, and to treat age-related disorders by administering modulators of the AMPK metabolic pathway, without stating whether it involves an activator or an inhibitor.

Saha et al. (Biochem. Biophys. *Res.* Commun 2006, 349:519-524) studied the AMPK-regulated growth of keratinocytes and conclude that AMPK activators such as AICAR promote the in vitro differentiation of keratinocytes.

Moreover, it is also accepted that extrinsic factors such as ultraviolet radiation, smoking or certain treatments (glucocorticoids, vitamin D and derivatives, for example) also have an effect on the skin and its collagen content.

Thus, prolonged exposure to ultraviolet radiation, particularly to type A and B radiation, has the effect of stimulating the expression of collagenases, particularly of MMP1 (also known as matrix metalloproteinase 1 or else interstitial collagenase), constituting one of the components of photoinduced or non-photoinduced skin ageing.

A certain number of active agents have already been proposed for preventing and/or treating the signs of skin ageing.

It is thus known practice to use specific hydroxylated compounds in order to stimulate collagen synthesis and/or the proliferation of fibroblasts of the dermis, as described in French application FR 2 777 186.

Moreover, as previously mentioned, skin ageing may be photoinduced, that is to say it may be caused following exposure to the sun. This extrinsic ageing is then called photoageing or dermatoheliosis.

Conversely, "conventional" ageing is sometimes called "chronological ageing" or "intrinsic ageing".

Keratin materials, and in particular the skin, are exposed daily to sunlight. As it happens, it is known that prolonged exposure of keratin materials, and in particular of the skin, to this polychromatic light is capable of inducing skin disorders or else superficial damage. This is in particular due to the formation of free radicals, reactive oxygen species such as $O_2^-$ and $HO\cdot$, which can damage DNA, certain lipids and/or proteins, and more generally which induce cell ageing. These reactive species disrupt biological mechanisms by inducing oxidative stress. This contributes to the development and acceleration of cell degeneration.

The production of reactive oxygen species therefore causes damage to DNA, to proteins and/or to lipids, and contributes to the acceleration of ageing of the cells of the skin in particular.

Thus, the effects of oxidative stress affect cell respiration and result in an accelerated ageing of the skin, accompanied in particular by a dull and/or grey complexion, an uneven complexion, a loss of radiance and/or transparency of the skin, the premature formation of wrinkles or fine lines, and a loss of softness, suppleness and elasticity of the skin.

Thus, UV radiation induces a phenomenon termed "photoageing", in particular of the skin, which includes as associated signs the appearance of wrinkles/fine lines, a loss of radiance and an unevenness of the complexion, a loss of firmness, and the appearance of roughness and of yellowing of the skin.

Exposure to the sun induces peroxidation of the surface lipids of the skin and/or of the scalp and in particular photoinduced peroxidation of lipids of sebaceous origin, such as squalene. It is in fact known that lipids which are at the surface of the skin, of the scalp and of the hair are continuously subjected to external attacks, and in particular the air, atmospheric pollutants and visible radiation and especially ultraviolet (UV) radiation, and that the most exposed to external attacks are those contained in the fatty secretions of the skin, such as sebum, which is rich in squalene. The presence in the squalene molecules of six double bonds makes these molecules sensitive to oxidation phenomena. Thus, during prolonged exposure to UV radiation, squalene becomes photoperoxidized to give squalene peroxides. This high production of squalene peroxides causes in particular a series of chain degradations, in particular in and on the skin, giving rise to numerous skin disorders including photoageing.

Numerous agents or treatments for preventing and/or treating photoageing already exist, such as vitamin A, botulinum toxin, skin filling agents, various laser treatments, dermabrasion and peels.

In addition, numerous antioxidants, used in the cosmetics industry for combatting free radicals, are already known.

The role of antioxidants is to capture and neutralize free radicals by converting them into subspecies which are of no danger to keratin materials.

Antioxidants can therefore be used in various fields, such as anti-ageing cosmetics, and protection against oxidative stress and in particular that caused by exposure to the sun.

Mention may particularly be made of vitamin E (alpha-tocopherols and isomers), vitamin C (ascorbic acid) and its derivatives, carotenoids, aminoindoles, melatonin, ubiquinone, coenzyme Q, green tea, thiols and their derivatives (glutathione, N-acetylcysteine), oligomeric proanthocyanidins (OPCs), flavonoids, catechins, in particular epicatechin and also its gallic derivatives, polyphenols, for instance tyrosol, hydroxytyrosol, sesamol, carnosol, gamma-orizanol, acids such as dihydrolipoic acid, uric acid, ferulic acid, caffeic acid, rosmarinic acid or carnosic acid, and also trans-resveratrol.

However, there remains a constant need to have available new active agents capable of exerting a beneficial cosmetic action on the signs of skin ageing, in particular the chronological signs, or of photoageing, and also a protective action on keratin materials against the effects of UV radiation, in particular for combatting free radicals.

It is an object of the present invention to meet this need.

Thus, according to a first subject, the present invention relates to the cosmetic use of at least one compound of formula (I) and/or solvates thereof and/or stereoisomers thereof:

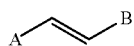
(I)

in which groups A and B are different and:
A-* represents a disubstituted phenyl radical:

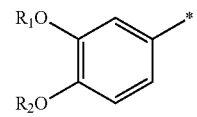

in which $R_1$ and $R_2$ are such that:
$R_1$ denotes a hydrogen atom or a linear or branched $C_1$-$C_4$ alkyl radical,
$R_2$ denotes a hydrogen atom, a linear or branched $C_1$-$C_4$ alkyl radical or a linear or branched $C_2$-$C_4$ acyl radical,
B-** represents a mono- or disubstituted phenyl radical:

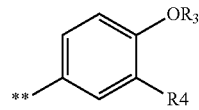

in which $R_3$ and $R_4$ are such that:
$R_3$ denotes a hydrogen atom, a linear or branched $C_1$-$C_4$ alkyl radical or a linear or branched $C_2$-$C_4$ acyl radical,
$R_4$ denotes a hydrogen atom or an OR4' radical with R4' denoting a hydrogen atom or a linear or branched $C_1$-$C_4$ alkyl radical,
the symbols * and ** indicating the sites of bonding on the ethylene respectively of the groups A and B,
or of a composition comprising, in a physiologically acceptable medium, at least one compound of formula (I) and/or solvates thereof and/or stereoisomers thereof,
for treating and/or preventing the signs of ageing and/or of photoageing of keratin materials, preferably of the skin.

The $R_1$, $R_2$, $R_3$ and $R_4$ radicals are chosen independently of one another.

In particular, the present invention is directed towards the cosmetic use of a compound of formula (I) and/or solvates thereof and/or stereoisomers thereof as an agent for treating and/or preventing the signs of ageing and/or of photoageing of keratin materials, preferably of the skin.

In particular, said composition or said compound is used as a photoprotective agent for keratin materials, in particular as an antioxidant.

According to a second subject, the present invention relates to a compound of formula (II):

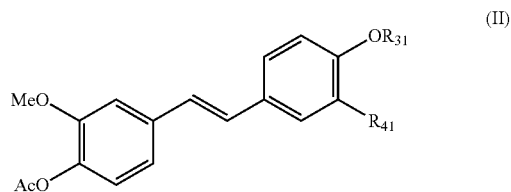
(II)

in which $R_{31}$ and $R_{41}$ are such that:
$R_{31}$ denotes a hydrogen atom or a linear or branched $C_1$-$C_4$ alkyl radical,
$R_{41}$ denotes a hydrogen atom or an $OR_{41}'$ radical, with $R_{41}'$ denoting a hydrogen atom or a linear or branched $C_1$-$C_4$ alkyl radical,
with the proviso that, when $R_{31}$ denotes a methyl group, then $R_{41}'$ does not denote a methyl group, and also solvates thereof and/or stereoisomers thereof, the compound of formula (II) preferably being a diastereoisomer of E configuration.

The $R_1$, $R_2$, $R_3$ and $R_4$ radicals are chosen independently of one another.

According to a third subject, the present invention relates to a cosmetic composition comprising, in a physiologically acceptable medium, at least one compound of formula (I) and/or solvates thereof and/or stereoisomers thereof, in particular a cosmetic composition comprising at least one compound of formula (I) and/or solvates thereof and/or stereoisomers thereof and at least one additive chosen from mineral or organic oils and/or surfactants and/or emulsifiers and/or thickeners and/or preservatives and/or fragrances.

In particular, the present invention relates to a cosmetic composition comprising, in a physiologically acceptable medium, at least one compound chosen from compounds 1 to 6, and in particular a cosmetic composition comprising at least one compound chosen from compounds 1 to 6 and at least one additive chosen from mineral or organic oils and/or surfactants and/or emulsifiers and/or thickeners and/or preservatives and/or fragrances.

According to a fourth subject, the present invention is directed towards a non-therapeutic cosmetic treatment process for keratin materials, in particular the skin, comprising the application, to the keratin materials, of a cosmetic composition comprising at least one compound of formula (I) and/or solvates thereof and/or stereoisomers thereof, and in particular a cosmetic composition comprising at least one compound chosen from compounds 1 to 6 and/or solvates thereof and/or stereoisomers thereof.

According to a fifth subject, the present invention relates to a composition, preferably a cosmetic composition, comprising, in a physiologically acceptable medium, at least one compound of formula (II).

According to a six subject, the present invention is directed towards a non-therapeutic cosmetic treatment process for keratin materials, in particular the skin, comprising the application, to the keratin materials, of a composition, preferably a cosmetic composition, comprising, in a physiologically acceptable medium, at least one compound of formula (II).

Against all expectations, the inventors have in fact demonstrated that the compounds of formula (I) have an anti-ageing activity and also a photoprotective activity.

The present invention will be understood more clearly on reading the description and the examples that follow.

For the purposes of the present invention and unless otherwise indicated, the term "compound of formula (I)" (respectively of formula (II)) is intended to mean a compound of formula (I) (respectively of formula (II)) as defined above and also solvates thereof and/or stereoisomers thereof.

For the purposes of the present invention, the term "keratin material" is intended to mean the skin, including the scalp.

For the purposes of the invention, the term "cosmetic use" is intended to mean a non-therapeutic use.

Anti-Ageing Activity

According to a first aspect, the present invention aims to protect the non-therapeutic cosmetic use of a composition containing, in a physiologically acceptable medium, at least one compound of formula (I) or (II) for preventing and/or treating ageing or photoageing of the skin, such as the skin of the face, of the neck, of the scalp, of the body and of the hands, and more preferentially the skin of the face or of the neck, said ageing or photoageing possibly being in particular linked to glycation, to skin homeostasis and/or to an increase in AMPK activity.

It is thus intended to target any modification of the outer appearance of the skin due to ageing, whether chronological and/or extrinsic, extrinsic ageing mainly being caused by physical or chemical attacks by the environment, which is manifested, for example, by wrinkles and fine lines, withered skin, flaccid skin, thinned skin, dull, lifeless skin, or lack of elasticity and/or of tonicity of the skin. For the purposes of the present description, extrinsic ageing is caused by physical or chemical attacks by the environment and mainly by UV radiation. Physical attacks by the environment include extreme temperatures.

Also according to this first aspect, the present invention relates to the prevention and/or treatment of wrinkles and/or fine lines and/or crevices, and of thinning of the skin.

According to the present invention, the term "treatment of wrinkles and/or fine lines" is intended to mean softening wrinkles and/or fine lines, or reducing the appearance of wrinkles and/or fine lines.

In addition, the compound of formula (I) used according to the invention makes it possible to combat the loss of firmness and/or of elasticity and/or of tonicity and/or of suppleness and/or the slackening of the skin, and also the radiance of the complexion.

Thus, the present invention relates to the improvement of the firmness of the skin, in particular of mature and/or wrinkled skin, and/or the radiance of the complexion.

The present invention also aims to protect a non-therapeutic cosmetic skin treatment process for treating and/or preventing the signs of skin ageing, in particular chronological signs, comprising at least one step consisting in applying, to the skin, a cosmetic composition comprising at least one compound of formula (I), the treated skin possibly exhibiting signs of skin ageing.

Photoprotective Activity

According to a second aspect, the present invention aims to protect the non-therapeutic cosmetic use of a composition containing, in a physiologically acceptable medium, at least one compound of formula (I) or (II) for protecting the skin against an oxidative stress caused by exposure of the skin to UV radiation, in particular for protecting the skin against an oxidative stress caused by repeated daily and/or prolonged exposure to UV radiation.

According to one variant of this second aspect, the composition also comprises at least one UV-screening agent.

The compositions according to the invention then contain at least one UV-screening agent. Preferably, the UV-screening agent suitable for the invention is chosen from water-soluble UV-screening agents, liposoluble UV-screening agents, insoluble UV-screening agents, and mixtures thereof, in particular water-soluble organic screening agents, liposoluble organic screening agents, insoluble organic screening agents, and inorganic screening agents.

Compounds of Formula (I) Used According to the Invention

As already mentioned, the invention relates to the non-therapeutic cosmetic use, as an agent for treating and/or preventing the signs of skin ageing, and/or as a photoprotective agent, in particular as an antioxidant, of a composition containing, in a physiologically acceptable medium, at least one compound of formula (I) and/or solvates and/or stereoisomers.

For the purposes of the invention, a $C_1$-$C_4$ alkyl radical is an alkyl group comprising from 1 to 4 carbon atoms, i.e. the alkyl group may comprise 1, 2, 3 or 4 carbon atoms.

Examples of alkyl groups that may be mentioned include methyl, ethyl, propyl, isopropyl, butyl, isobutyl and tert-butyl groups.

For the purposes of the invention, a $C_2$-$C_4$ acyl group is a group of formula:

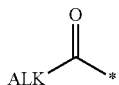

where ALK denotes a $C_1$-$C_3$ alkyl radical such as methyl, ethyl, propyl or isopropyl.

In particular, an acetyl group is a $CH_3CO$—* (Ac—*) group.

Preferably, the isomers according to the invention are stereoisomers, in particular enantiomers, diastereoisomers, and also mixtures thereof, including racemic mixtures.

According to one preferred variant, the compounds of formula (I) or (II) are chosen from the diastereoisomers of E configuration (trans).

The acceptable solvates of the compounds of formula (I) comprise conventional solvates. Mention may be made, by way of example, of the solvates due to the presence of water or of linear or branched alcohols, such as ethanol or isopropanol.

According to a first variant of the invention, the compound of formula (I) is characterized in that $R_1$ denotes a hydrogen atom or a methyl radical, preferably a methyl radical.

According to a second variant of the invention, the compound of formula (I) is characterized in that $R_2$ denotes a hydrogen atom, a methyl radical or an acetyl radical, preferably an acetyl radical.

According to a third variant of the invention, the compound of formula (I) is characterized in that $R_3$ denotes a hydrogen atom, a linear or branched $C_1$-$C_4$ alkyl radical or an acetyl radical, preferably a hydrogen atom, a methyl radical or an acetyl radical.

According to a fourth variant of the invention, the compound of formula (I) is characterized in that $R_4$ denotes a hydrogen atom or an $OR4'$ radical, with $R4'$ denoting a methyl group.

In particular, the compound of formula (I) used according to the invention is chosen from compounds 1 to 6 below:

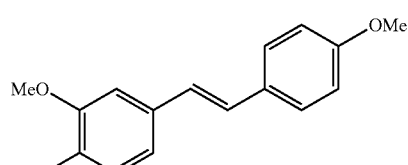

1

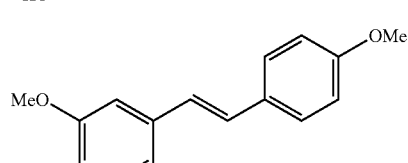

2

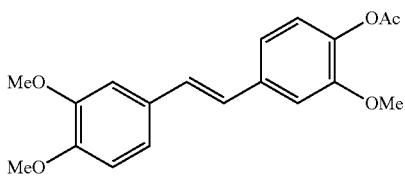

3

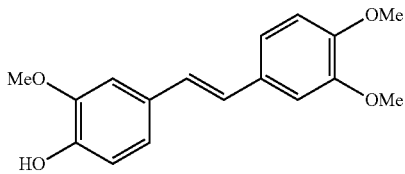

4

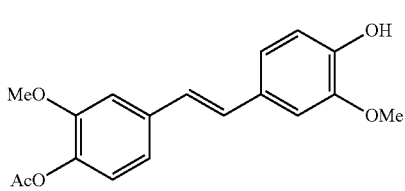

5

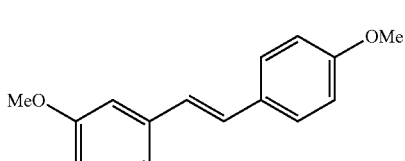

6 and also the stereoisomers and/or solvates thereof.

These compounds may be in the form of the Z and/or E diastereoisomers thereof; preferably, the compound of formula (I) is in the form of the diastereoisomer of E configuration.

Furthermore, according to a particular embodiment, the present invention relates to the cosmetic use of at least one compound of formula (I) and/or solvates thereof and/or stereoisomers thereof:

(I)

in which groups A and B are different and:

A-* represents a disubstituted phenyl radical:

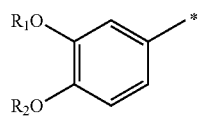

in which $R_1$ and $R_2$ are such that:

$R_1$ denotes a hydrogen atom or a linear or branched $C_1$-$C_4$ alkyl radical, $R_2$ denotes a hydrogen atom, a linear or branched $C_1$-$C_4$ alkyl radical or a linear or branched $C_2$-$C_4$ acyl radical, B-** represents a mono- or disubstituted phenyl radical:

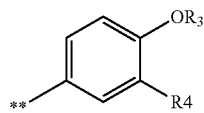

in which $R_3$ and $R_4$ are such that:
$R_3$ denotes a linear or branched $C_1$-$C_4$ alkyl radical, and
$R_4$ denotes an OR4' radical with R4' denoting a linear or branched $C_1$-$C_4$ alkyl radical,
the symbols * and ** indicating the sites of bonding on the ethylene respectively of the groups A and B,
or of a composition comprising, in a physiologically acceptable medium, at least one compound of formula (I) and/or solvates thereof and/or stereoisomers thereof, for treating and/or preventing the signs of ageing and/or of photoageing of keratin materials such as the skin, preferably for treating and/or preventing the signs of chronological ageing.

According to this particular embodiment, the compounds of formula (I) used for treating and/or preventing the signs of ageing and/or of photoageing of keratin materials, such as the skin, preferably for treating and/or preventing the signs of chronological ageing are compounds wherein $R_3$ denotes a methyl radical and $R_4$ denotes an OR4' radical with R4' denoting a methyl radical, more particularly the compound preferably used is compound 4:

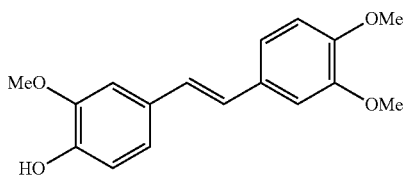

As already indicated, the present invention also relates to the novel compounds of formula (II):

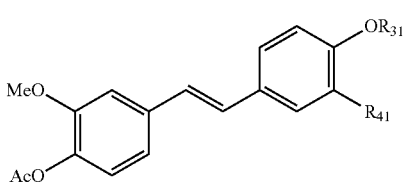

in which $R_{31}$ and $R_{41}$ are such that:
$R_{31}$ denotes a hydrogen atom or a linear or branched $C_1$-$C_4$ alkyl radical,
$R_{41}$ denotes a hydrogen atom or an $OR_{41}'$ radical, with $R_{41}'$ denoting a hydrogen atom or a linear or branched $C_1$-$C_4$ alkyl radical,
with the proviso that, when $R_{31}$ denotes a methyl group, then $R_{41}'$ does not denote a methyl group,
and also the stereoisomers and/or solvates thereof.
The compound of formula (II) is preferably in the form of the diastereoisomer of E configuration.
Preferably, the compound of formula (II) is such that:
$R_{31}$ denotes a hydrogen atom or a methyl group,
$R_{41}$ denotes a hydrogen atom or an OR41' radical with R41' denoting a hydrogen atom or a methyl group,
with the proviso that, when $R_{31}$ denotes a methyl group, then $R_{41}'$ does not denote a methyl group,
and also the stereoisomers and/or solvates thereof, preferably in the form of the diastereoisomer of E configuration.
More preferably, the compound of formula (II) is chosen from compounds 5 and 6 below:

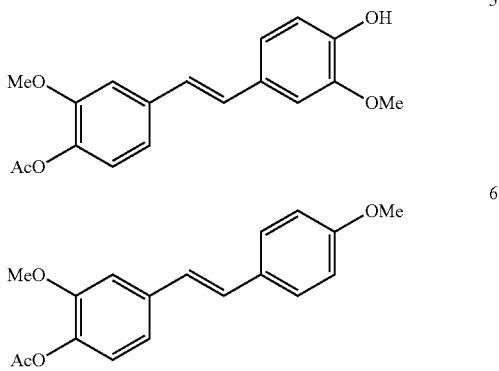

and also the stereoisomers and/or solvates thereof, preferably in the form of the diastereoisomer of E configuration.

Synthesis of the Compounds of Formulae (I) and (II)

The compounds of formulae (I) and (II) according to the invention can be obtained by cross metathesis reaction between the styrene (Ra and/or Rb=H) or corresponding β-methylstyrene (Ra and/or Rb=Me) derivatives Sa and Sb, as represented below:

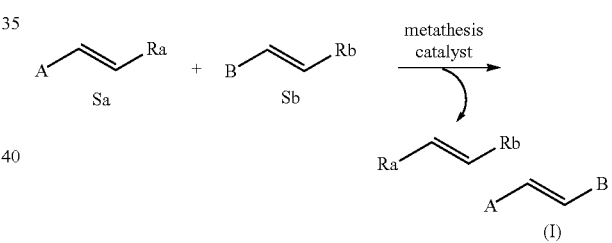

Ra = H or Me
Rb = H or Me

The precursors Sa (1-15 equiv.) and Sb (1-15 equiv.), used pure or diluted in an organic solvent such as dichloromethane or toluene, are brought into contact with a metathesis catalyst (0.0001-0.1 equiv.) such as the Grubbs II ruthenium complex or the Hoveyda-Grubbs ruthenium complex.

The reaction mixture is stirred for 5 min-24 h at a temperature of between 15 and 120° C. The solvent is then evaporated off under reduced pressure and the residue is purified using techniques well known to those skilled in the art, such as recrystallization, silica gel column chromatography or preparative thin layer chromatography.

Cosmetic Composition

A composition suitable for the invention, namely intended for the implementation of the invention, may be a cosmetic or dermatological composition according to the application envisaged, preferentially a cosmetic composition, and therefore comprises a physiologically acceptable medium.

The term "physiologically acceptable medium" is intended to mean a medium that is compatible with keratin materials such as the skin, the scalp, or any other area of bodily skin. A physiologically acceptable medium is preferentially a cosmetically or dermatologically acceptable medium, i.e. a medium that has no unpleasant odour, colour or appearance, and that is entirely compatible with the route of administration under consideration.

By way of example, a cosmetic composition used according to the present invention comprises an amount of between 0.001% and 30% by weight, preferably between 0.01% and 10% by weight, in particular between 0.5% and 5% by weight, relative to the total weight of the composition, of at least one compound of formula (I) or (II).

The composition according to the invention is intended for topical application.

The composition may also comprise any constituent usually used in the envisaged application.

Mention may be made in particular of water, solvents, oils of mineral or organic origin, waxes, pigments, fillers, surfactants, additional cosmetic active agents other than the compounds of formula (I) and/or (II), or else polymers. For example, the composition according to the invention may comprise at least one cosmetic adjuvant chosen, for example, from water; organic solvents, in particular $C_2$-$C_6$ alcohols and $C_2$-$C_{10}$ carboxylic acid esters; hydrocarbon-based oils, silicone oils, fluoro oils, waxes, pigments, fillers, dyes, surfactants, emulsifiers, UV-screening agents, film-forming polymers, hydrophilic or lipophilic gelling agents, thickeners, preservatives, fragrances, bactericides and odour absorbers.

In the composition according to the invention, the compounds (I) and/or (II) can also be used together with additional anti-ageing or photoprotective active agents other than the compounds of formula (I) and/or (II).

The composition according to the invention may also comprise at least one additional cosmetic active agent other than the compounds of formula (I) and/or (II), such as, for example, desquamating agents, moisturising agents, depigmenting or propigmenting agents, NO-synthase inhibitors, dermodecontracting agents, tensioning agents, and mixtures thereof.

Thus, the composition according to the invention may be in the form of an anti-ageing composition, in particular a care composition, for combatting the external signs of skin ageing and/or in the form of a photoprotective composition.

This composition may be in any galenical form normally used in the cosmetics field, and may in particular be in the form of an optionally gelled aqueous solution, a dispersion, optionally a two-phase dispersion, of the lotion type, an emulsion obtained by dispersing a fatty phase in an aqueous phase (O/W), or (W/O), or a triple (W/O/W or O/W/O) emulsion or a vesicular dispersion of ionic and/or non-ionic type.

The composition of the invention may constitute, for example, a lotion, a gel, a cream or a milk.

Thus, the composition may comprise any constituent usually used in the envisaged topical application and administration.

Needless to say, those skilled in the art will take care to select this or these optional additional compound(s), and/or the amount thereof, such that the advantageous properties of the compound of formula (I) or (II) used according to the invention are not, or are not substantially, adversely affected by the envisaged addition, and such that the properties of the compositions resulting therefrom are compatible with the topical route.

A composition according to the invention may be in the form of a face and/or body care or makeup product, and may be conditioned, for example, in the form of cream in a jar or of fluid in a tube or in a pump-action bottle.

According to one preferred embodiment, a composition according to the invention comprising at least one compound of formula (I) or (II) of the invention is formulated in an anti-ageing cream and/or in a cream for photo protection.

A composition according to the invention may be manufactured via any known process generally used in the cosmetics field.

Cosmetic Processes

The present invention also relates to a non-therapeutic cosmetic treatment process for keratin materials, in particular the skin, comprising the application, to said materials, of a composition as defined according to the invention.

The present invention also relates to a process for cosmetic treatment and/or for prevention of the appearance of the signs of skin ageing, characterised in that a cosmetic composition containing at least one compound of formula (I) and/or a compound of formula (II) as defined in the present description is applied to the skin.

In certain embodiments of these processes, the composition is applied to mature and/or wrinkled skin.

The non-therapeutic cosmetic process of the invention is performed by topically administering a composition in accordance with the invention.

The topical administration consists of the external application, to the keratin materials, in particular the skin, of cosmetic compositions according to the usual technique for using these compositions.

By way of illustration, the cosmetic process according to the invention can be performed by application, for example daily, of a composition in accordance with the invention, which may be formulated, for example, in the form of a cream, gel, serum, lotion, emulsion, makeup-removing milk or aftersun composition.

According to another embodiment, the application is repeated, for example 2 to 3 times daily for one day or more and generally for an extended period of at least 4 weeks, or even 4 to 15 weeks with, where appropriate, one or more periods of stoppage.

According to a particular embodiment of the invention, other agents intended to make the appearance and/or the texture of the skin more attractive may also be added to the composition according to the invention.

The present invention also relates to the non-therapeutic use of a cosmetic composition as defined previously, for cosmetically preventing and/or treating the signs of skin ageing and/or for providing a photoprotective effect, such as an antioxidant effect.

The invention also relates to the non-therapeutic use of a composition as defined in the present description, for improving the firmness of the skin.

Throughout the description, including the claims, the expression "comprising a" should be understood as being synonymous with "comprising at least one", unless otherwise specified.

The expressions "between . . . and . . . " and "ranging from . . . to . . . " should be understood as being inclusive of the limits, unless otherwise specified.

The examples and figures that follow are presented as non-limiting illustrations of the invention.

EXAMPLES

Synthesis of the Compounds of Formula (I)

Example 1: Compound 1

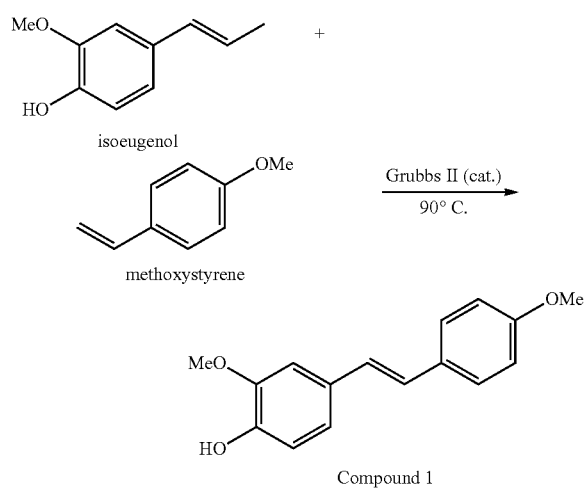

Methoxystyrene (410 mg, 3.0 mmol, 1 equiv.) and isoeugenol (1.0 g, 6.1 mmol 2 equiv.) are introduced into a round-bottomed flask. The Grubbs catalyst (2nd generation, 8 mg, 0.009 mmol, 0.003 equiv.) is added at ambient temperature. The reaction mixture is then stirred at 90° C. under an argon stream for 30 minutes. During the reaction, solidification is observed.

After purification of the reaction crude dissolved in acetone, by preparative thin layer chromatography on a silica support, compound 1 is isolated in the form of a slightly grey powder.

The $^1$H NMR spectrum complies with the expected structure.

Example 2: Compound 4

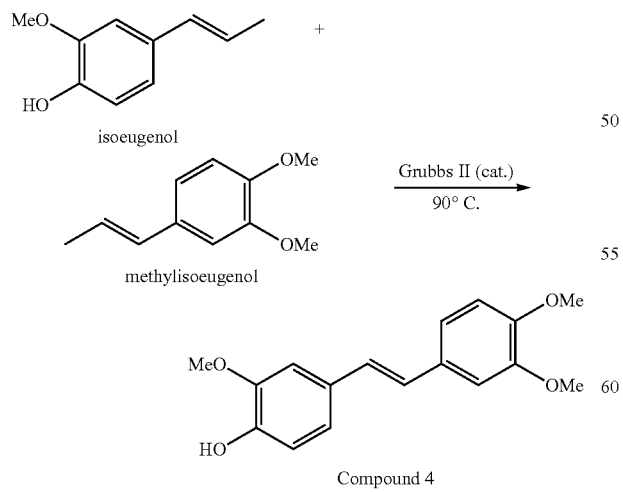

Methylisoeugenol (1.1 g, 6.1 mmol, 1 equiv.) and isoeugenol (1.0 g, 6.1 mmol 1 equiv.) are introduced into a round-bottomed flask. The Grubbs catalyst ($2^{nd}$ generation, 5 mg, 0.006 mmol, 0.001 equiv.) is added at ambient temperature. The reaction mixture is then stirred at 90° C. under an argon stream for 30 minutes. During the reaction, solidification is observed.

After purification of the reaction crude dissolved in acetone, by preparative thin layer chromatography on a silica support, compound 4 is isolated in the form of a white powder.

The $^1$H NMR spectrum complies with the expected structure.

Synthesis of the Novel Compounds of Formula (II)

The compounds of formula (II) according to the invention can be obtained by cross metathesis reaction between isoeugenyl acetate and the corresponding 3-methylstyrene BM, as represented below:

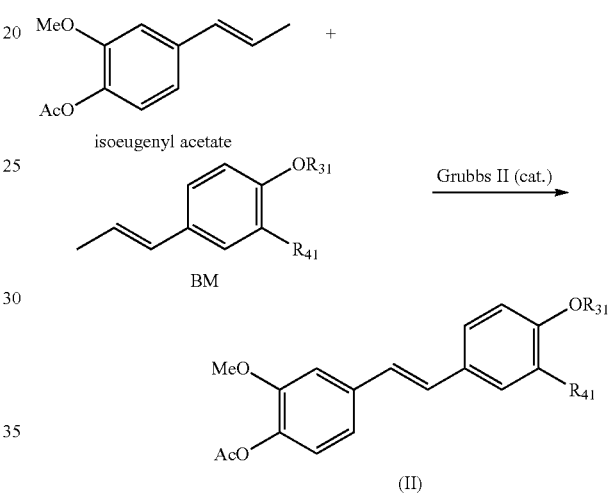

The isoeugenyl acetate (1-15 equiv.) and the β-methylstyrene BM (1-15 equiv.), used pure or diluted in an organic solvent such as dichloromethane or toluene, are brought into contact with a metathesis catalyst (0.0001-0.1 equiv.) such as the Grubbs II ruthenium complex or the Hoveyda-Grubbs ruthenium complex.

The reaction mixture is stirred for 5 min-24 h at a temperature of between 15 and 120° C. The solvent is then evaporated off under reduced pressure and the residue is purified by recrystallization, preparative thin layer chromatography or silica gel column chromatography.

Example 3: Compound 5

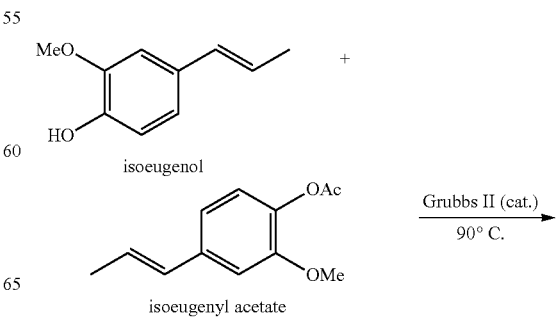

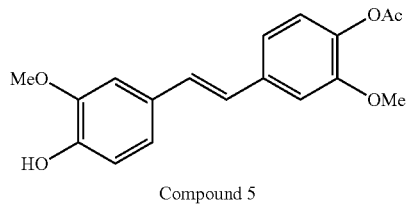

Compound 5

Isoeugenol (1.0 g, 6.1 mmol, 1 equiv.) and isoeugenyl acetate (1.3 g, 6.1 mmol 1 equiv.) are introduced into a round-bottomed flask. The Grubbs catalyst ($2^{nd}$ generation, 5 mg, 0.006 mmol, 0.001 equiv.) is added at ambient temperature. The reaction mixture is then stirred at 90° C. under an argon stream for 30 minutes. During the reaction, solidification is observed.

After purification of the reaction crude dissolved in acetone, by preparative thin layer chromatography on a silica support, compound 5 is isolated in the form of a white powder.

The $^1$H NMR spectrum complies with the expected structure.

Example 4: Example of Composition in Accordance with the Invention

The percentages of compounds shown are percentages by weight, relative to the total weight of the composition in which they are present.

| | |
|---|---|
| Compound 5 | 1% |
| Glycerol | 12% |
| Polyacrylamide at 40% AM (Sepigel 305 from SEPPIC) | 1% AM |
| Preservatives | qs |
| Fragrance | qs |
| Water | qs 100% |

The composition above, applied topically to the skin, makes it possible to combat signs of ageing caused by an oxidative stress in the skin due to UV exposure, such as wrinkles and fine lines, or else thinned skin.

Example 5: Activity of the Compounds

I. Production of Reactive Oxygen Species (ROS)

A. Materials and Methods

The decrease of the production of reactive oxygen species in keratinocytes of the HaCaT line is evaluated by detection, using the Dihydrorhodamine 123 (DHR123) probe or using Dichloro-dihydro-fluorescein diacetate (DCFH-DA) probe, the ROS production is induced by exposition to UVA after 24 h of incubation in the presence of the compounds to be tested.

The DHR123 and DCFH-DA probes are indicators of the presence of reactive oxygen species (ROS).

B. Procedure

HaCaT keratinocytes in monolayer culture are placed in the presence of a solution of a compound to be tested at various concentrations (0.4-200 μM) in the medium.

After 24 h of incubation, the cells are exposed to UVA, then incubated with the DHR123 probe or DCFH-DA probe for 1 h. The fluorescence of the probe is then measured. A viability test is carried out in parallel in order to discard the cytotoxic compounds.

In parallel, the keratinocytes are incubated with vitamin C acting as a positive control and a standard: an incubation with 500 μM of vitamin C corresponds to 100% photoprotection.

The dose-effect curves of the fluorescence detected as a function of the concentration of compounds (to be tested) present in the medium make it possible to calculate the effective dose $EC_{50}$ which corresponds to the concentration of compound (to be tested) that allows 50% photoprotection of the keratinocytes.

C. Results

The results are represented in Table 1 below.

TABLE 1

| Compound | $EC_{50}$-DHR123 | $EC_{50}$-DCFH-DA | ROS production decrease |
|---|---|---|---|
| 1 | 36 μM | 20 μM | Yes |
| 5 | ND | 29 μM | Yes |
| 4 | 100 μM | ND | Yes |

"ND" meaning "non detected"

Thus, compounds of general chemical formula (I) are capable, on a cell assay at micromolar doses, of preventing the formation of reactive species induced by exposure to UVA.

In a cosmetic formulation, they are therefore effective for delaying and/or reducing the harmful effects of an oxidative stress in the skin due to exposure to UV, the signs of which can result, in the short term in an erythema, and in the long term, in an unevenness and a loss of radiance of the complexion, a slackening of the skin tissues and a loss of tone (firmness) of the skin, the appearance of wrinkles and grooves, a rough and yellowish appearance, an uneven complexion or the appearance of telangiectasia.

II. Evaluation on AMPK pathway

A. Principle

Evaluation of the effect of compound 4 on the AMPK pathway in NHEK cells (Normal Human Epidermal Keratinocytes) by analysis of the pACC (Acetyl-CoA Carboxylase) phosphorylated form expression. This effect is studied by fluorescent immunolabeling and image analysis.

B. Procedure

Keratinocytes are seeded in 96-well microplates and grown for 24 hours in a culture medium. The medium is then replaced by the test medium and cells are grown for 24 supplementary hours. Finally, the medium is replaced by the test medium comprising or not (control) the tested compounds, the reference (AICAR) or the control solvent (0.1% or 0.5% DMSO) then the cells are incubated for 48 hours. All the test conditions were carried out with n=3.

After incubation, the immunolabeling is done. The results are expressed in labeling % of the pACC compared to the control brought back to 100%.

The results are represented in Table 2 below.

TABLE 2

| Tested compound | concentration | % control | SEM(%) | p |
|---|---|---|---|---|
| control | — | 100 | 1 | — |
| reference AICAR | 500 μM (0.5% DMSO) | 117 | 5 | * |
| Compound 4 | 10 μM | 119 | 4 | ** |

SEM: standard error of mean
p: statistic significance threshold
* 0.01 to 0.05: significant
** 0.001 to 0.01: very significant.

Compound 4, at 10 μM concentration, is capable of inducing a global increase of the pACC labelling (+19%) that is of the same order than the AICAR reference at 500 μM (+17%).

Compound 4, at a relatively low concentration (10 μM), is then capable to active the AMPK route in normal human keratinocytes.

The invention claimed is:

1. A method for treating signs of aging and/or photoaging of a skin, comprising:
applying to said skin at least one compound of formula (I) and/or solvates thereof and/or stereoisomers thereof:

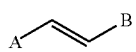

(I)

in which groups A and B are different and:
A-* represents a disubstituted phenyl radical:

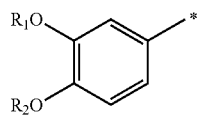

in which $R_1$ and $R_2$ are such that:
$R_1$ denotes a linear or branched $C_1$-$C_4$ alkyl radical,
$R_2$ denotes a hydrogen atom, a linear or branched $C_1$-$C_4$ alkyl radical or a linear or branched $C_2$-$C_4$ acyl radical,
B-** represents a mono- or disubstituted phenyl radical:

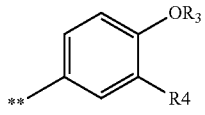

in which $R_3$ and $R_4$ are such that:
$R_3$ denotes a hydrogen atom, a linear or branched $C_1$-$C_4$ alkyl radical or a linear or branched $C_2$-$C_4$ acyl radical,
$R_4$ denotes a hydrogen atom or an $OR_{4'}$ radical with $R_{4'}$ denoting a hydrogen atom or a linear or branched $C_1$-$C_4$ alkyl radical,
the symbols * and ** indicating the sites of bonding on the ethylene respectively of the groups A and B,
or of a composition comprising, in a physiologically acceptable medium, at least one compound of formula (I) and/or solvates thereof and/or stereoisomers thereof.

2. The method according to claim 1, comprising applying to the skin at least one compound of formula (I) in which $R_1$ denotes a methyl radical.

3. The method according to claim 1, comprising applying to the skin at least one compound of formula (I) in which $R_2$ denotes a hydrogen atom, a methyl radical or an acetyl radical.

4. The method according to claim 1, comprising applying to the skin at least one compound of formula (I) in which $R_3$ denotes a hydrogen atom, a linear or branched $C_1$-$C_4$ alkyl radical or an acetyl radical.

5. The method according to claim 1, comprising applying to the skin at least one compound of formula (I) in which $R_4$ denotes a hydrogen atom or an $OR_{4'}$ radical, with $R_{4'}$ denoting a methyl group.

6. The method according to claim 1, comprising applying to the skin at least one compound of formula (I) chosen from the compounds below:

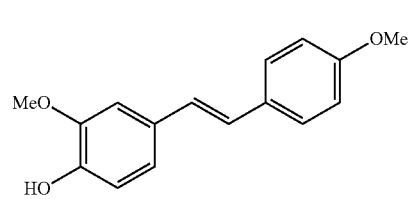

1

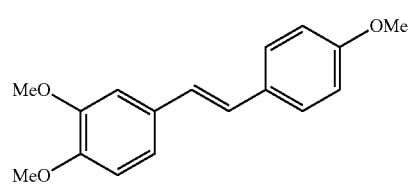

2

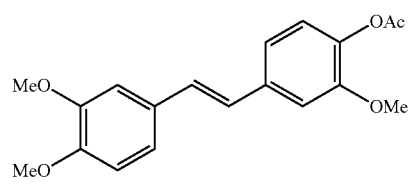

3

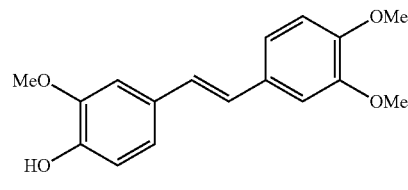 [SMILES: COc1cc(/C=C/c2ccc(OC)c(OC)c2)ccc1O]

4

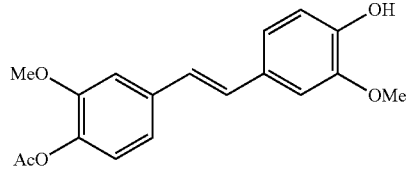

5

-continued

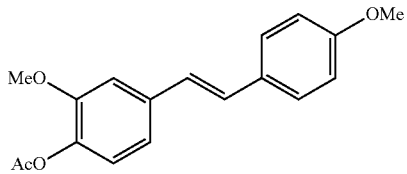

and the solvates and/or stereoisomers thereof.

7. The method according to claim 6, wherein the at least one compound of formula (I) is a diastereoisomer of E configuration.

8. The method according to claim 1, comprising applying to the skin at least one compound of formula (I) in which $R_3$ and $R_4$ are such that $R_3$ denotes a linear or branched $C_1$-$C_4$ alkyl radical, and $R_4$ denotes an $OR_{4'}$ radical with $R_{4'}$ denoting a linear or branched $C_1$-$C_4$ alkyl radical.

9. The method according to claim 1, wherein the at least one compound of formula (I) is compound 4:

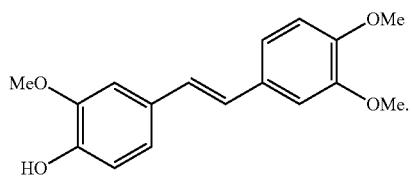

10. The method according to claim 1, for treating wrinkles and/or fine lines and/or crevices, and thinning of the skin.

11. The method according to claim 1, for improving the firmness of the skin and/or the radiance of the complexion.

12. The method according to claim 1, as a photoprotective agent for the skin.

13. The method according to claim 12, for protecting the skin against an oxidative stress caused by exposure of the skin to UV radiation.

14. The method according to claim 12, for protecting the skin against an oxidative stress caused by repeated daily and/or prolonged exposure to UV radiation.

15. The method according to claim 12, in which the composition comprises at least one UV-screening agent.

16. A method for protecting a skin against an oxidative stress caused by exposure of the skin to UV radiation, comprising:
applying to said skin at least one compound of formula (I) and/or solvates thereof and/or stereoisomers thereof:

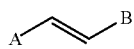 (I)

in which groups A and B are different and:
A-* represents a disubstituted phenyl radical:

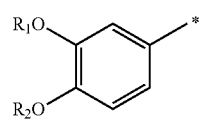

in which $R_1$ and $R_2$ are such that:
$R_1$ denotes a linear or branched $C_1$-$C_4$ alkyl radical,
$R_2$ denotes a hydrogen atom, a linear or branched $C_1$-$C_4$ alkyl radical or a linear or branched $C_2$-$C_4$ acyl radical, B-** represents a mono- or disubstituted phenyl radical:

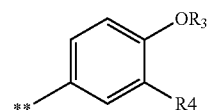

in which $R_3$ and $R_4$ are such that:
$R_3$ denotes a hydrogen atom, a linear or branched $C_1$-$C_4$ alkyl radical or a linear or branched $C_2$-$C_4$ acyl radical,
$R_4$ denotes a hydrogen atom or an $OR_{4'}$ radical with $R_{4'}$ denoting a hydrogen atom or a linear or branched $C_1$-$C_4$ alkyl radical, the symbols * and ** indicating the sites of bonding on the ethylene respectively of the groups A and B, or of a composition comprising, in a physiologically acceptable medium, at least one compound of formula (I) and/or solvates thereof and/or stereoisomers thereof.

17. A compound of formula (II)

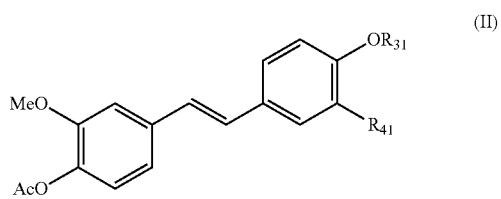 (II)

in which $R_{31}$ and $R_{41}$ are such that:
$R_{31}$ denotes a hydrogen atom or a methyl group,
$R_{41}$ denotes a hydrogen atom or an $OR_{41'}$ radical, with $R_{41'}$ denoting a hydrogen atom or a linear or branched $C_1$-$C_4$ alkyl radical,
with the proviso that, when $R_{31}$ denotes a methyl group, then $R_{41'}$ does not denote a methyl group,
and the solvates and/or stereoisomers thereof.

18. The compound of formula (II) according to claim 17, in which:
$R_{31}$ denotes a hydrogen atom or a methyl group,
$R_{41}$ denotes a hydrogen atom or an $OR_{41'}$ radical with $R_{41'}$ denoting a hydrogen atom or a methyl group,
with the proviso that, when $R_{31}$ denotes a methyl group, then $R_{41'}$ does not denote a methyl group,
and the solvates and/or stereoisomers thereof.

19. The compound of formula (II) according to claim 17, which is chosen from:

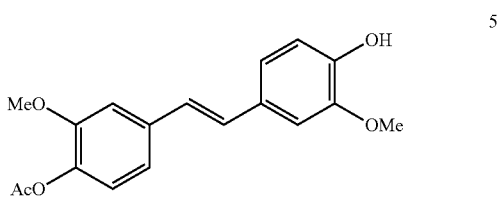

-continued

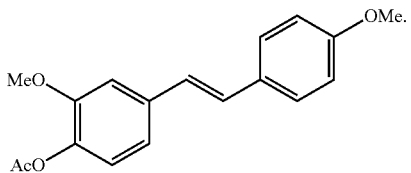

20. Composition A composition comprising, in a physiologically acceptable medium, at least one compound of formula (II) as defined in claim 17.

21. The composition according to claim 20, comprising an amount of between 0.001% and 30% by weight, relative to the total weight of the composition, of at least one compound of formula (II).

22. The composition according to claim 20, being a cosmetic composition, in which the physiologically acceptable medium comprises at least one cosmetic adjuvant chosen from water; organic solvents, hydrocarbon-based oils, silicone oils, fluoro oils, waxes, pigments, fillers, dyes, surfactants, emulsifiers, cosmetic active agents, UV-screening agents, film-forming polymers, hydrophilic or lipophilic gelling agents, thickeners, preservatives, fragrances, bactericides, odour absorbers and antioxidants.

23. A cosmetic treatment process for the skin, comprising applying, to said skin the composition as defined in claim 20.

24. The cosmetic treatment process for the skin according to claim 23, for treating the signs of skin ageing and/or protecting keratin materials, against the effects of UV radiation.

25. A cosmetic composition comprising, in a physiologically acceptable medium, at least one compound of formula (I) as defined in claim 1 and/or solvates thereof and/or stereoisomers thereof, and at least one additive chosen from mineral or organic oils and/or surfactants and/or emulsifiers and/or thickeners and/or preservatives and/or fragrances.

* * * * *